US00PP27654P2

(12) United States Plant Patent
Traven

(10) Patent No.: US PP27,654 P2
(45) Date of Patent: Feb. 7, 2017

(54) ***FARFUGIUM* PLANT NAMED 'WAVY GRAVY'**

(50) Latin Name: *Farfugium japonicum*
Varietal Denomination: Wavy Gravy

(71) Applicant: Lloyd Traven, Kintnersville, PA (US)

(72) Inventor: Lloyd Traven, Kintnersville, PA (US)

(73) Assignee: B & S PLANTS, LLC, Kintnersville, PA (US)

( * ) Notice: Subject to any disclaimer, the term of this patent is extended or adjusted under 35 U.S.C. 154(b) by 55 days.

(21) Appl. No.: 14/545,876

(22) Filed: Jun. 30, 2015

(51) Int. Cl.
*A01H 5/12* (2006.01)

(52) U.S. Cl.
USPC ..... Plt./448

(58) Field of Classification Search
USPC ..... Plt./448
See application file for complete search history.

*Primary Examiner* — Anne Grunberg
(74) *Attorney, Agent, or Firm* — Penny J. Aguirre

(57) ABSTRACT

A new cultivar of *Farfugium japonicum* plant named, 'Wavy Gravy', that is characterized by its compact, uniform, round mounded plant habit, its young puberulent foliage that remains densley pubescent even when fully expanded, its extremely tightly curled foliage that is gray-green in color, and its stems that are long and straight in shape.

2 Drawing Sheets

Botanical classification: *Farfugium japonicum.*
Cultivar designation: 'Wavy Gravy'.

BACKGROUND OF THE INVENTION

The present invention relates to a new and distinct cultivar of *Farfugium*, botanically known as *Farfugium japonicum* 'Wavy Gravy' and hereinafter referred to by its cultivar name 'Wavy Gravy'. The new cultivar of *Farfugium japonicum* is a herbaceous perennial grown for ornamental landscape and container use.

The Inventor discovered the new cultivar in the summer of 2013 as a naturally occurring branch mutation *Farfugium japonicum* (not patented) growing in his trial garden in Kintnersville, Pa.

Asexual propagation of the new cultivar was first accomplished by division by the Inventor in Kintnersville, Pa. in December of 2013. Asexual propagation of the new cultivar by division and tissue culture has shown that the unique features of 'Wavy Gravy' are stable and reproduced true to type in successive generations.

SUMMARY OF THE INVENTION

The following traits have been repeatedly observed and represent the characteristics of the new cultivar. These attributes in combination distinguish 'Wavy Gravy' as a new and unique cultivar of *Farfugium.*

1. 'Wavy Gravy' exhibits a compact, uniform, round mounded plant habit.
2. 'Wavy Gravy' exhibits young puberulent foliage that remains densley pubescent even when fully expanded.
3. 'Wavy Gravy' exhibits very tightly curled foliage that is gray-green in color.
4. 'Wavy Gravy' exhibits stems that are long and straight in shape.

The parent plant of 'Wavy Gravy' differs from 'Wavy Gravy' in having leaves that are flat in aspect with a curly maring, in having foliage that is more green in color, leaves that are less pubescent, stems that are not as straight or strong, and in having a less uniform plant habit. 'Wavy Gravy' can be most closely compared to the *Farfugium japonica* cultivars 'Aureomaculata' (not patented) and 'Gigantea' (not patented). 'Aureomaculata' differs from 'Wavy Gravy' in having leaves that are larger in size, glossy, glabrous, dark green with yellow markings in color, flat instead of curly, entire margins, and in having an inconsistent and open plant habit. 'Gigantea' differs from 'Wavy Gravy' in being larger in overall size and in having leaves that are dark green in color.

BRIEF DESCRIPTION OF THE DRAWINGS

The accompanying colored photographs illustrate the overall appearance and distinct characteristics of the new *Farfugium*. The photographs were taken of a nine month-old plant (from a division) of 'Wavy Gravy' as grown outdoors in a one-gallon container in Kintnersville, Pa.

The photograph in FIG. 1 provides a side view of the plant habit of 'Wavy Gravy'.

Figure 1:
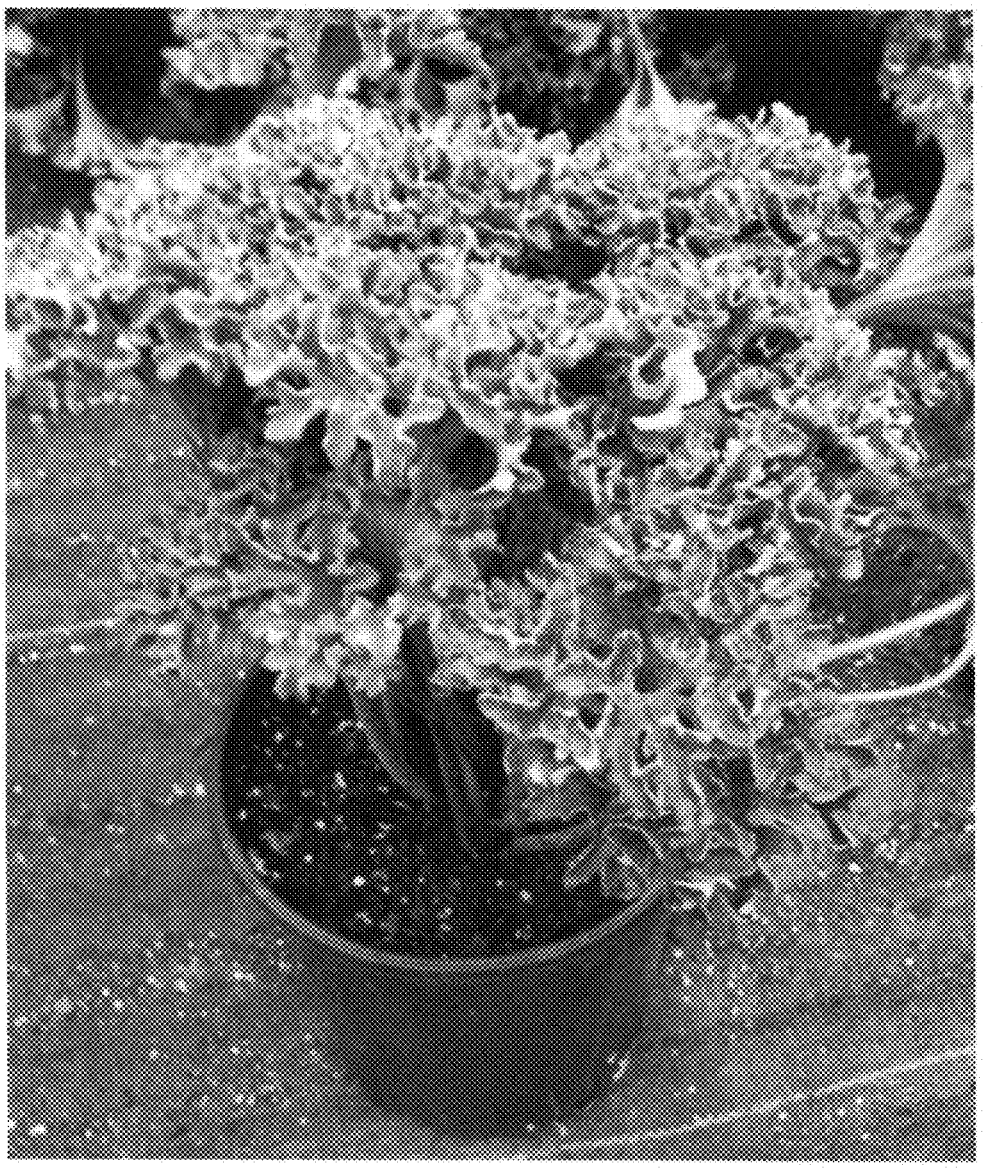
Figure 2:
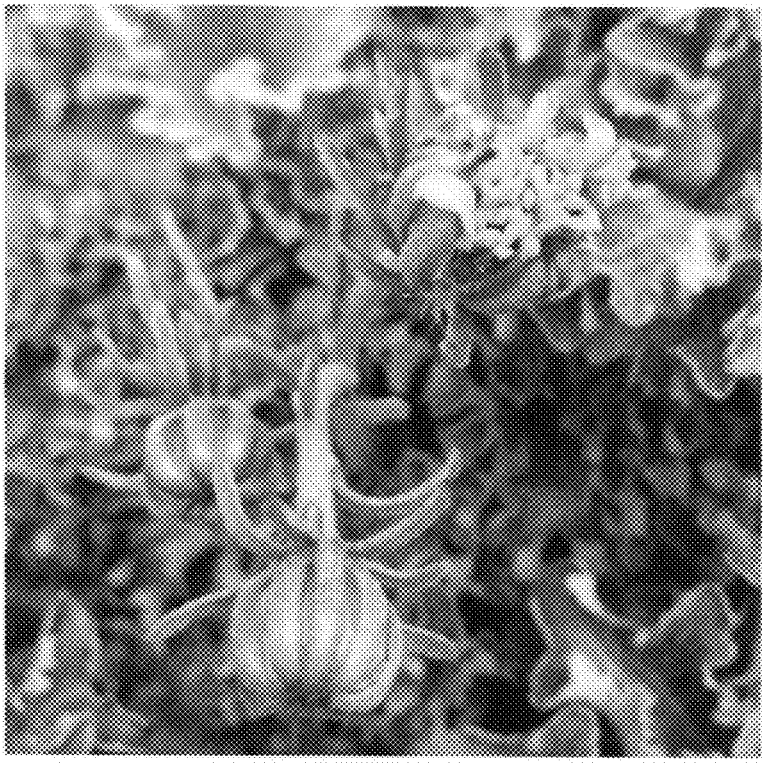

The photograph in FIG. 2 provides a close-up view of an inflorescence and inflorescence buds of 'Wavy Gravy'.

Figure 3:
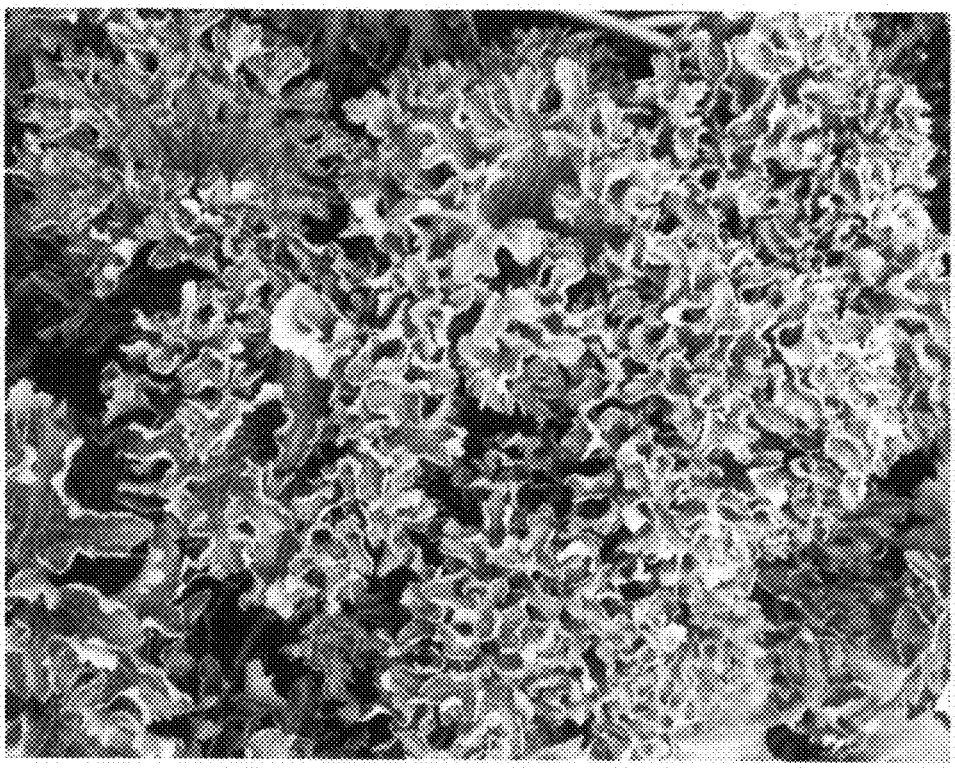

The photograph in FIG. 3 provides a close-up view of the foliage of 'Wavy Gravy'.

The colors in the photographs are as close as possible with the digital photography techniques available, the color values cited in the detailed botanical description accurately describe the colors of the new *Farfugium.*

DETAILED BOTANICAL DESCRIPTION

The following is a detailed description of nine month-old plants (from a division) of the new cultivar as grown outdoors in a one-gallon container in Kintnersville, Pa. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—Blooms inconsistently from late spring to early summer in Pennsylvania.

*Plant type*.—Herbaceous perennial.

*Plant habit*.—Compact, clump forming, round and mounded.

*Height and spread*.—An average of 45 cm in height and 60 cm in spread.

*Hardiness*.—U.S.D.A. Zone 7.

*Diseases and pests*.—Observed to be disease and pest free under the conditions tested.

*Root description*.—Fibrous.

*Branching habit*.—Stemless except for flowering stems, long petioles arise from crown.

*Propagation*.—In vitro propagation (preferred) and division.

*Growth rate*.—Moderate to vigorous.

Foliage description:

*Leaf shape*.—Reniform.

*Leaf division*.—Simple.

*Leaf base*.—Sagitate.

*Leaf apex*.—Obtuse.

*Leaf venation*.—Palmate, conspicuous on upper surface, color on upper surface 138C, color on lower surface 138B with the veins near the base a blend of 176B and 183C (petiole color).

*Leaf margins*.—Lobed with secondary lobes on lobes, highly ruffled.

*Leaf attachment*.—Petiolate.

*Leaf arrangement*.—Basal rosette.

*Leaf orientation*.—Held upright on petiole, fanned out on all sides at about a 45° angle, extreme ruffling of margins gives a circular appearance.

*Leaf surface*.—Upper surface is satiny, lower surface dull and puberulent, both surfaces sparsely covered with loosely held wooly hairs.

*Leaf color*.—Young and mature upper surface; 191B, young and mature lower surface; a blend of 138A and 138B.

*Leaf size*.—Up to 12 cm in width and 8 cm in length.

*Leaf quantity*.—An average of 32 in a one-gallon container.

*Petioles*.—Oval in shape with sulcate, held primarily upright, an average of 20 cm in length and 5 mm in width on mature leaves, a blend of 176B and 183C in color, surface is satiny and sparsely convered with lossely held wooly hairs.

Inflorescence description:

*Type*.—Capitulum, heterogamous with a few ray pistillate florets with primarily perfect disk florets, non showy, forming a cup-shaped head, arranged in pairs at terminus on unbranched flowering scape.

*Capitulum number*.—An average of 2 per flowering stem.

*Lastingness of inflorescence*.—About 1 week.

*Capitulum size*.—An average of 2 cm in depth and 2.5 cm in diameter, no distinct disk portion.

*Fragrance*.—Very slight.

*Phyllary*.—Arranged in 3 rows, 144A in color with very apex 187A on upper and lower surfaces, outer row; an average of 4, 144A in color on both surface, linear-lancelate in shape, about 9 mm in length and 2 mm in width, glabrous on upper surface, wooly pubecence on lower surface, truncate base, acuminate apex, inner overlapping rows; about 10, form a campanulate involucre about 1 cm in length and 1.2 cm in width, mucrinate acute apex is about 2 mm in length and width, color is 144A with apex 187A, both surfaces are glossy with slightly wooly pubescence on outer surface.

*Buds*.—Globose in shape, an average of 1 cm in diameter and depth, 144A in color with very apex 187A, slightly pubwscent surface.

*Peduncle* (*flowering stem*).—Emerges from crown, an average of 26 cm in length and 5 mm in width, a blend of 176B and 183C in color and blending into 138B and 177D near apex, surface is moderately covered with lossely held wooly hairs 177D in color, an average of 2 leaves on upper porition, sessile, linear in shape with clasping base and blunt apex, wooly pubescent on both surfaces.

*Pedicels*.—An average of 3 cm in length and an average of 3 mm in width, color is 177D in color due to surface that is heavily tomentose, 1 to 3 leaves; lancelate in shape, up to 1.5 cm in length and 3 mm in width, 138B on upper and lower surface, satiny and glabrous on upper surface and pubescent on lower surface.

*Ray florets* (*female*).—An average of 5, about 1 cm in length and 5 mm in width, single petal; oblanceolate in shape, about 8 mm in length and 3 mm in width and narrow base about 7 mm in length and 1 mm in width, oblanceolate in shape, rounded apex with single notch, attenuate base, entire margin except apex, glabrous upper and lower surface, slightly reflexed, color of upper and lower surface 2B, pappus portion about 8 mm in length and 4 mm in width, and primarily 197A in color.

*Disk flowers* (*bisexual*).—About 40, tubular in shape, arranged vertically on flat receptacle, about 1.8 cm in length and 5 mm in width, tube portion 2B in color and 5 mm in length and 2 mm in width, pappus portion about 8 mm in length and 4 mm in width, and primarily 197A in color, recepticle; 7 mm in diameter and 2 mm in depth, surface is 155A in color.

Reproductive organs:

*Gynoecium*.—Pistil; 1, about 1 cm in length and 2 mm in width, style; 6 mm in length, 145D in color, surrounded by stamens, stigma; bifid, each arm is reflexed and about 1 mm in length and 2B in color, ovary; inferior, about 2 mm in length, 1.5 mm in width, and 145D in color.

*Androcoecium*.—Stamens; about 10, un-fused, coherent in cylinder around style, anthers; 2 to 3 mm in length and 0.3 mm in width, basifixed, 199A in color, filaments; 3 mm in length, thin and wiry, pollen; not readily distinguishable.

*Fruit*.—Development not observed.

It is claimed:

1. A new and distinct cultivar of *Farfugium japonicum* plant named 'Wavy Gravy' as herein illustrated and described.

* * * * *